United States Patent [19]

Ludwig et al.

[11] Patent Number: 5,206,269

[45] Date of Patent: Apr. 27, 1993

[54] HIGHLY CONCENTRATED AMINO ACID SOLUTION

[75] Inventors: Josef K. Ludwig, Vernon Hills; Douglas G. Johnson, Grayslake, both of Ill.

[73] Assignee: Clintec Nutrition Co., Deerfield, Ill.

[21] Appl. No.: 854,227

[22] Filed: Mar. 20, 1992

[51] Int. Cl.⁵ ............................................ A61K 31/195
[52] U.S. Cl. ................................... 514/561; 514/562
[58] Field of Search .................................. 514/561, 562

[56] References Cited

U.S. PATENT DOCUMENTS

| | | | |
|---|---|---|---|
| 5,026,721 | 6/1991 | Dudrick | 514/561 |
| 5,032,608 | 7/1991 | Dudrick | 514/561 |
| 5,051,249 | 9/1991 | Metcoff | 514/561 |

Primary Examiner—Marianne M. Cintins
Assistant Examiner—John Peabody
Attorney, Agent, or Firm—Hill, Steadman & Simpson

[57] ABSTRACT

The present invention provides a nutritionally useful highly concentrated amino acid solution. In an embodiment, the formulation has a broad amino acid profile that is both high in branched chain amino acids and high in overall percent of amino acids. Additionally, the present invention provides a method of selecting the amino acid profile so as to obtain a maximum amino acid concentration. To this end, a stable amino acid solution having a nutritionally appropriate balance of amino acids comprising a total amino acid concentration equal to or greater than 18% (wt/vol) is provided. In an embodiment, an amino acid solution is provided comprising approximately 18 to about 22% branched chain amino acids (wt/wt); and a total amino acid concentration equal to or greater than 18% (wt/vol).

15 Claims, No Drawings

HIGHLY CONCENTRATED AMINO ACID SOLUTION

BACKGROUND OF THE INVENTION

The present invention relates generally to solutions for providing nutrition to patients. More specifically, the present invention relates to amino acid solutions.

It is known to provide amino acids in parenteral solutions to patients. These solutions can be utilized for total parenteral nutrition (TPN). Examples of such solutions include 10%, 8.5%, 5.5%, and 3.5% Travasol ® (amino acid) injection, with and without electrolytes, available from Clintec Nutrition Company, Deerfield, Ill.

It is also known to provide branched chain amino acids, i.e., isoleucine, leucine, and valine in parenteral solutions. An example of such a product is 4% Branchamin (branched chain amino acid) injection available from Clintec Nutrition Company, Deerfield, Ill.

For a variety of medical reasons, e.g., fluid restricted patients, it is desirable to have an amino acid solution for TPN that is as concentrated as possible. Of course, such a solution must have the appropriate nutritional balance. Likewise, for convenience reasons, e.g., volume of stock and transportation, it is desirable to have a TPN solution having as great an amino acid concentrated as possible.

Presently, the highest concentration amino acid solution for TPN that is available, to the best of the inventors' knowledge, is a 15% (wt/vol) solution. Although attempts have been made to provide higher concentrated amino acid solutions, these attempts have not been entirely successful.

One previous practice for attempting to develop an amino acid solution of increased concentration was to simply increase the amino acid components. However, this practice does not work when the components of a 15% formulation are increased proportionally. Merely increasing the amino acids proportionally will cause the amino acids to begin to precipitate out of solution.

One approach to attempt to solve this problem is to increase the total amino acid concentration by loading up the mixture with the amino acids that are most soluble. Using this method, conversely the less soluble amino acids are not increased in any significant amount. However, the result of this approach is an amino acid solution which, while perhaps more concentrated, is not nutritionally useful.

It is also desirable to have a solution that is highly concentrated in branched chain amino acids as well as amino acids. Presently, the only way to obtain such a solution is to admix a branched chain amino acid solution, e.g., 4% Branchamin ®, with another amino acid solution which has a broad amino acid profile, e.g., Travasol ®. However, by so admixing a highly concentrated amino acid solution is not achieved. Further, a single stable solution that can be stored is not provided through this method.

SUMMARY OF THE INVENTION

The present invention provides a nutritionally useful highly concentrated amino acid solution. In an embodiment, the formulation has a broad amino acid profile that is both high in branched chain amino acids and high in overall percent of amino acids.

Additionally, the present invention provides a method of selecting the amino acid profile so as to obtain a maximum amino acid concentration.

To this end, a stable amino acid solution having a nutritionally appropriate balance of amino acids comprising a total amino acid concentration equal to or greater than 18% (wt/vol) is provided.

In an embodiment, an amino acid solution is provided comprising: approximately 18 to about 22% branched chain amino acids (wt/wt); and a total amino acid concentration equal to or greater than 18% (wt/vol).

In an embodiment, a high concentration amino acid solution is provided comprising: at least the amino acids leucine, isoleucine, valine, glutamic acid, aspartic acid, lysine, histidine, arginine, phenylalanine, methionine, threonine, alanine, glycine, proline, serine; the ratio (wt/wt) of glutamic acid, aspartic acid, lysine, histidine, and arginine to phenylalanine, methionine, threonine, alanine, glycine, proline, and serine being 0.57 to 0.65; and the ratio (wt/wt) of glutamic acid, aspartic acid, lysine, histidine, and arginine to phenylalanine, methionine, threonine, alanine, glycine, proline, serine, leucine, isoleucine, and valine being approximately 0.45.

In an embodiment, a high concentration amino acid solution is provided comprising: at least 18% (wt/vol) amino acid concentration; a ratio of amino acids having a pI (isoelectric point) of 5-7 to amino acids having a pI outside the range of 5-7 (excluding branched chain amino acids and those amino acids present in a wt/vol of less than or equal to 2%) of 0.57 to 0.65 by weight.

A method of making a high concentration amino acid solution is also provided by the present invention.

Numerous advantages are achieved by the present invention. The resultant amino acid solution is more concentrated by at least 33% than currently available amino acid solutions. The solution can comprise greater than or equal to 18% branched chain amino acids with greater than or equal to 45% essential amino acids.

The increased concentration allows the amino acid solution to be used with fluid restricted patients while providing necessary nutrition. Additionally, lower shipping and storage mass provides for reduced costs for the same amino acid equivalents. The increased composition is accomplished without sacrificing the concentration of branched chain amino acids or the percent of essential amino acids.

Additional features and advantages of the present invention are described in, and will be apparent from, the detailed description of the presently preferred embodiments.

DETAILED DESCRIPTION OF THE PRESENTLY PREFERRED EMBODIMENTS

The present invention provides a highly concentrated amino acid solution that provides a nutritionally effective amino acid profile. A method for determining maximum amino acid concentration vis-a-vis amino acid profile is also provided.

To this end, a stable amino acid solution having a nutritionally appropriate balance of amino acid is provided comprising at least a total amino acid concentration equal to or greater than 18% (wt/vol). This is a 33% increase over the previously most concentrated solutions available, i.e., a 15% concentration.

Pursuant to the present invention, amino acids are classified based on their pI values (isoelectric point) as well as percent concentration of the composition. Most amino acids are thereby classified as being of type 1 or type 2.

Pursuant to the present invention, the maximum amino acid concentration is obtained when the ratio of type 1 to type 2 amino acids is in a certain range. Values outside the range are either not stable or do not represent the highest amino acid concentration for the amino acid mixture.

Pursuant to the present invention, 20% (wt/vol) amino acid solutions can be achieved. Furthermore, by using these values, a stable product can be more rapidly obtained.

Pursuant to the method of the present invention, amino acids are classified. These classifications are utilized, instead of working with the individual amino acids in the mixture, to control the character of the solution to determine maximum stability. This immensely simplifies the process because instead of having to determine the maximum solubilities of individual amino acids in the presence or absence of other amino acids, the solubilities of groups of the amino acids can be determined at different ratios.

The increased ease is easy to appreciate by merely appreciating that in typical solutions, 17 amino acids may be present. Using previous methods of increasing concentrations, an individual amino acid's solubility had to be compared against 16 other amino acids. Pursuant to the present invention, only one group of amino acids needs to be compared to the other group of amino acids.

It is easy to determine the value for any formulation beyond which the formulation will not be stable pursuant to the present invention.

The value that is used to determine the maximum concentration is a reflection of the nature of the matrix of the amino acid solution. In this complex mixture, there are many physical and chemical principles at work pushing the stability of the solution in different directions.

At a low amino acid concentration, i.e., 15% or less wt/vol, the characteristics of the matrix are not critical. However, when the concentration increases and some of the amino acids are present at levels above their solubility in water alone, the characteristics become an important parameter for obtaining a stable solution.

Some physiochemical properties of the amino acids are set forth below.

| AMINO ACID ABBREVIATIONS | |
| --- | --- |
| Amino Acid | Abbreviation |
| Leucine | LEU |
| Isoleucine | ILE |
| Valine | VAL |
| Phenylalanine | PHE |
| Methionine | MET |
| Lysine | LYS |
| Threonine | THR |
| Tryptophan | TRP |
| Histidine | HIS |
| Alanine | ALA |
| Glycine | GLY |
| Arginine | ARG |
| Proline | PRO |
| Tyrosine | TYR |
| Serine | SER |
| Aspartic Acid | ASP |
| Glutamic Acid | GLU |

PHYSIOCHEMICAL PROPERTIES[1,2]

| Amino Acid | Mol/ Wt | Sol g/ 100 g H2O at 25° C. | pI | pk1 | pK2 | pK3 | TYPE (4) |
| --- | --- | --- | --- | --- | --- | --- | --- |
| LEU | 131.11 | (2)2.33 | 5.98 | 2.36 | 9.60 | | E, BC |
| ILE | 131.11 | 4.12 | 5.94 | 2.26 | 9.62 | | E, BC |
| VAL | 117.09 | 8.85 | 5.96 | 2.32 | 9.62 | | E, BC |
| PHE | 165.19 | 2.97 | 5.48 | 1.83 | 9.13 | | E |
| MET | 149.15 | 3.38 | 5.74 | 2.28 | 9.21 | | E |
| LYS | 146.19 | V. SOL | 9.59 | 2.20 | 8.90 | 10.28 | E |
| THR | 119.08 | 20.50 | 6.16 | 2.71 | 9.62 | | E |
| TRP | 204.22 | 1.14 | 5.89 | 2.38 | 9.29 | | E |
| HIS | 155.16 | 4.29 | 7.59 | 1.78 | 5.97 | 9.17 | E |
| ALA | 89.09 | 16.72 | 6.00 | 2.34 | 9.69 | | NE |
| GLY | 75.07 | 24.99 | 5.97 | 2.34 | 9.60 | | NE |
| ARG | 174.20 | (3)15.0 | 11.15 | 2.18 | 9.04 | 12.84 | NE |
| PRO | 115.08 | 162.30 | 6.30 | 1.99 | 10.60 | | NE |
| TYR | 181.19 | 0.05 | 5.66 | 2.20 | 9.11 | 10.07 | NE |
| SER | 105.06 | 5.02 | 5.68 | 2.21 | 9.15 | | NE |
| ASP | 133.07 | 0.50 | 2.77 | 1.88 | 3.65 | 9.60 | NE |
| GLU | 147.08 | 0.84 | 3.22 | 2.19 | 4.32 | 9.67 | NE |

(1) To be used as the acetate salt. The weight of lysine acetate is 1.41 times the weight of lysine.
(2) At 35° C.
(3) At 21° C.
(40 BC- Branch Chain, E - Essential, NE - Non-Essential The inventors have found a system of classifying the amino acids into groups (type 1, type 2, and others) so that one is able to develop the most likely formulation having the highest concentration without having to investigate the effect of each individual component of the less than or equal to 15% amino acid concentration likely to be a part of the formulation.

To develop a solution with so many components wherein the limiting factor is keeping of the material in solution would require an extensive matrix of solubilities of individual amino acids and numerous solutions with varying concentrations of each component. Even with this information, the stability of the formulation would be in doubt because of unknown relationships between the effect of the presence of one amino acid on the solubility of not only the amino acid of interest, but also of that for all the other entities of the solution.

The inventors have identified four types of amino acids and the relative ratios that are important in determining the profile of a high concentration amino acid solution. These amino acids are classified as: Type 1, Type 2, Branched Chain, and Special. The categories are assigned as follows: Special Amino Acids are those wherein the concentration of the specific amino acid is less than or equal to 2%. wt/wt of the amino acids; Branched Chain Amino Acids are, of course, leucine, isoleucine, valine; Type 1 Amino Acids are those having a pI value (isoelectric point) between 5 and 7 (non-ionic group); and Type 2 Amino Acids are those having a pI value (isoelectric point) outside of the range 5–7 (ionic group).

The amounts of each amino acid in each group are determined based on the desired nature of the amino acid formulation. The inventors have determined the branched chain amino acid concentration as well as the ratio of Type 1 to Type 2 amino acids that will yield the maximum concentration of amino acids as well as the maximum branched chain amino acid concentration that can be obtained without the overall amino acid concentration dropping beneath 20% (wt/vol).

It was found that preferably, the maximum branched chain amino acid concentration in a 20% wt/vol amino acid solution has a Type 1/Type 2 ratio by weight of approximately 0.62. The solution is also characterized by a value of Type 1/Type 2 +branched chain amino acid of approximately 0.45.

It has been found that only a formulation with a Type 1/Type 2 ratio value of approximately 57 to about 0.65 (wt/wt) will be stable. Although not every such formulation may be stable, the inventors have found that one can eliminate from consideration any formulation that does not fall within this range.

By way of example, and not limitation, examples of the present invention will now be set forth.

EXAMPLE NO. 1

A formulation A, set forth below, was created.

Formulation A was found to percipitate amino acids leucine, isoleucine, methionine, phenylalanine, and valine in experiments.

The solution was modified in order to decrease the ionic character of the solution. The most ionic species, lysine and glutamic acid were deceased. Decreasing the amount of lysine also decreased the amount of acetate. Glutamic acid was also decreased to lower the ionic character of the solution and to bring the concentration closer to its solubility in water. Glutamic acid has a solubility at 25° C. of 0.84 grams per 100 ml. The amino acids that were increased were the amino acids that were more non-ionic and highly soluble. These were glycine, serine, and proline.

| | FORMULATION CHANGE: | | | |
|---|---|---|---|---|
| Amino Acid | Formula A | Percent of Total (g/100 ml) | Formula B | Percent of Total |
| LEU | 1.240 | 6.20 | 1.080 | 5.40 |
| ILE | 1.240 | 6.20 | 1.080 | 5.40 |
| VAL | 1.520 | 7.60 | 1.440 | 7.20 |
| PHE | 1.200 | 6.00 | 1.000 | 5.00 |
| MET | 0.900 | 4.50 | 0.760 | 3.80 |
| LSY[(1)] | 1.570 | 7.85 | 1.350 | 6.75 |
| THR | 1.000 | 5.00 | 0.980 | 4.90 |
| TRP | 0.325 | 1.63 | 0.320 | 1.80 |
| HIS | 1.190 | 5.95 | 1.180 | 5.90 |
| ALA | 2.750 | 13.75 | 2.760 | 13.80 |
| GLY | 1.380 | 6.90 | 2.060 | 10.30 |
| ARG | 1.950 | 9.75 | 1.960 | 9.80 |
| PRO | 1.200 | 6.00 | 1.340 | 6.70 |
| TYR | 0.050 | 0.25 | 0.050 | 0.25 |
| SER | 0.785 | 3.93 | 1.020 | 5.10 |
| ASP | 0.600 | 3.00 | 0.600 | 3.00 |
| GLU | 1.100 | 5.50 | 1.020 | 5.10 |
| % BC | 20.0 | | 18.0 | |
| % ES | 50.7 | | 46.0 | |

[(1)]Lysine added as the acetate salt.

Following the hypothesis that the formulation A was too ionic, it was believed that the percipitating amino acids could be kept in solution by changing (lowering) the ionic character of the mix. In order to do this most effectively, the amino acids were divided into the following four groups: (1) Branched Chain amino acids, (2) Special amino acids, (3) Non-Ionic amino acids and (4) Ionic amino acids.

The Branched Chain amino acids are leucine, isoleucine, and valine. The Special amino acids are tyrosine and tryptophan. They are in a separate group because their amounts could not be changed with respect to the other amino acids. The Non-Ionic group consists of amino acids whose isoelectric point was between 5.0 and 7.0. The remaining amino acids were grouped into the Ionic category. It was calculated that the formulation A contained 32.05% (wt/wt) "Ionic" amino acids and the B formulation consisted of 30.5%.

To prove this theory and develop he best formulation, with the highest branch chain concentration, four further modifications of the B formulation were derived. Two formulations with 20% (wt/wt) branched chain amino acids, increased proportionally to the B formulation, were derived.

In one formulation, the difference in branched chain amino acid weight (an increase of 0.4 grams per 100 ml) was compensated by a proportional decrease in the Ionic group (B20H) and in the other with a decrease in the Non-ionic group (B20L). Two other formulations were derived by decreasing the branch chain group from 18% (wt/wt) in formulation B18 to 16% (wt/wt) branched chain amino acids. This loss was made up by an increase in the Ionic group (B16L) or by an increase of the Non-ionic group (B16H). The formulations were named according to the formulation (B), the percent branch chain (16, 18 or 20) and the relative amount of the Non-ionic group (H—high or L—low).

| B FORMULATIONS: | | | | | |
|---|---|---|---|---|---|
| | FORMULATIONS | | | | |
| AMINO ACIDS | B16L (mg/100 ml) | B16H | B18 | B20H | B20L |
| BRANCHED CHAIN | | | | | |
| LEU | 960 | 960 | 1080 | 1200 | 1200 |
| ILE | 960 | 960 | 1080 | 1200 | 1200 |
| VAL | 1280 | 1280 | 1440 | 1600 | 1600 |
| TOTAL | 3200 | 3200 | 3600 | 4000 | 4000 |
| IONIC | | | | | |
| GLU | 1087 | 1020 | 1020 | 953 | 1020 |
| ASP | 639 | 600 | 600 | 561 | 600 |
| LYS[(1)] | 1438 | 1350 | 1350 | 1262 | 1350 |
| HIS | 1257 | 1180 | 1180 | 1103 | 1180 |
| ARG | 2088 | 1960 | 1960 | 1832 | 1960 |
| TOTAL | 6510 | 6110 | 6110 | 5710 | 6110 |
| NON-IONIC | | | | | |
| PHE | 1000 | 1040 | 1000 | 1000 | 960 |
| MET | 760 | 791 | 760 | 760 | 729 |
| THR | 980 | 1020 | 980 | 980 | 940 |
| ALA | 2760 | 2871 | 2760 | 2760 | 2649 |
| GLY | 2060 | 2143 | 2060 | 2060 | 1977 |
| PRO | 1340 | 1394 | 1340 | 1340 | 1286 |
| SER | 1020 | 1061 | 1020 | 1020 | 979 |
| TOTAL | 9920 | 10320 | 9920 | 9920 | 9520 |
| INSOLUBLE | | | | | |
| TYR | 50 | 50 | 50 | 50 | 50 |
| TRP | 320 | 320 | 320 | 320 | 320 |
| TOTAL | 370 | 370 | 370 | 370 | 370 |
| % BC | 16.0 | 16.0 | 18.0 | 20.0 | 20.0 |
| % ES | 44.7 | 44.5 | 45.9 | 47.1 | 47.4 |

[(1)]Lysine added as lysine acetate.

SOLUBILITY EXPERIMENT Blends were prepared of branched chain, ionic and non-ionic amino acids and from these blends 200 ml of each of the five B formulations were prepared with the separate addition of tyrosine and tryptophan. Amino acids were added to water heated to 80° C. and 0.5ml of acetic acid was added. The solutions were stirred for 30 minutes and cooled. The solution of formulation B20H had a small amount of undissolved material floating on the surface after 30 minutes at 80° C. All five solutions were cooled to 25° C. in an ice bath, the pH was adjusted to 6.0 with acetic acid and the volume was adjusted to 200 ml. The solutions were filtered through a 0.2μ membrane filter. Two 100ml portions of each solution were sealed into 100 ml glass bottles. One set was stored at 5° C. and the other at 25° C.

After one week, all solutions were checked for precipitates. Flakes floating on top of the solution were apparent in the B20L sample stored at 25° C. All other solutions stored at 25° C. and all stored at 5° C were clear. After two weeks, the only precipitated solution was still the B20L. There was a ring of material along the glass at the top of the liquid. All the solutions stored at 25° and 5° C., except the B20L at 25° C., were clear after three weeks.

This experiment proved that the overall solubility could be increased by lessening the ionic nature of the solution. Formulations containing 20% (wt/wt) branched chain amino acids could be produced.

EXAMPLE NO. 2

Four compositions C-F were created to determine stability. The compositions included branched chain amino acids. The ratio of types (ROT) of the amino acids are set forth below as well as stabilities. The composition includes 18% wt/wt of the total amino acids as branched chains amino acids and the total concentration of amino acids was varied.

| Form. | % (wt/v) Total Amino Acid | ROT(½) | ROT(1/(2 + BC)) | Stable |
|---|---|---|---|---|
| C | 20.05% | 0.62 | 0.454 | yes |
| D | 20.38% | 0.65 | 0.480 | no |
| E | 20.54% | 0.59 | 0.439 | no |
| F | 21.08% | 0.62 | 0.457 | yes |

Although this experiment demonstrated that not all compositions having a ROT(1/2) ratio of 0.57 to 0.65 are stable, the inventors did determine that compositions at a highly concentrated range of 21.08% that fall within this range were stable.

EXAMPLE NO. 3

The following amino acid solutions were created and found to be stable.

| | Test Article Formulation: FORMULATIONS | | | | |
|---|---|---|---|---|---|
| Amino Acids | B18 (g/l) | C20-1A (g/l) | C20-1B (g/l) | C20-2A (g/l) | C20-2B (g/l) |
| Branch Chain | | | | | |
| Leucine | 10.80 | 10.50 | 10.50 | 10.50 | 10.50 |
| Isoleucine | 10.80 | 11.50 | 11.50 | 11.50 | 11.50 |
| Valine | 14.40 | 18.00 | 18.00 | 18.00 | 18.00 |
| Ionic | | | | | |
| Glutamic Acid | 10.20 | 9.95 | 10.20 | 9.20 | 9.20 |
| Aspartic Acid | 6.00 | 5.85 | 6.00 | 4.00 | 4.00 |
| Lysine | 13.50 | 13.16 | 13.50 | 13.60 | 13.94 |
| Histidine | 11.80 | 11.51 | 11.80 | 11.90 | 12.19 |
| Arginine | 19.60 | 19.10 | 19.60 | 19.80 | 20.24 |
| Non-Ionic | | | | | |
| Phenylalanine | 10.00 | 9.75 | 9.60 | 9.00 | 9.00 |
| Methionine | 7.60 | 7.41 | 7.30 | 6.50 | 6.50 |
| Threonine | 9.80 | 9.56 | 9.40 | 9.90 | 9.76 |
| Alanine | 27.60 | 26.90 | 26.50 | 27.80 | 27.46 |
| Glycine | 20.60 | 20.09 | 19.75 | 20.80 | 20.50 |
| Proline | 13.40 | 13.07 | 12.85 | 13.50 | 13.35 |
| Serine | 10.20 | 9.95 | 9.80 | 10.30 | 10.16 |
| Special | | | | | |
| Tyrosine | 0.50 | 0.50 | 0.50 | 0.50 | 0.50 |
| Tryptophan | 3.20 | 3.20 | 3.20 | 3.20 | 3.20 |
| Amino Acid (g/l) Total | 200.00 | 200.00 | 200.00 | 200.00 | 200.00 |
| Percent (wt/wt) | | | | | |
| Branch Chain | 18.00 | 20.00 | 20.00 | 20.00 | 20.00 |
| Essential | 0.460 | 0.473 | 0.474 | 0.471 | 0.473 |
| Ratio | | | | | |
| I/N | 0.616 | 0.616 | 0.642 | 0.598 | 0.616 |
| I/(N + BC) | 0.452 | 0.436 | 0.452 | 0.425 | 0.436 |

I = Ionic Amino Acids (Type 1)
N = Nonionic Amino Acids (Type 2)

The first formula (B18) above, a 20% (wt/vol) amino acid formulation with 18% (wt/wt) branch chain amino acids was found to be stable for at least twelve months.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A stable amino acid solution having a nutritionally appropriate balance of amino acids comprising a total amino acid concentration equal to or greater than 18% (wt/vol), the solution including ionic and nonionic amino acids, and wherein the ratio (wt/wt) of nonionic to ionic amino acids, excluding branched chain amino acids, is 0.57 to 0.65.

2. The stable amino acid solution of claim 1 wherein the amino acid profile is approximately as follows:

| | (g/l) |
|---|---|
| Leucine | 10.50 |
| Isoleucine | 11.50 |
| Valine | 18.00 |
| Glutamic Acid | 9.20 |
| Aspartic Acid | 4.00 |
| Lysine | 13.94 |
| Histidine | 12.19 |
| Arginine | 20.24 |
| Phenylalanine | 9.00 |
| Methionine | 6.50 |
| Threonine | 9.76 |
| Alanine | 27.46 |
| Glycine | 20.50 |
| Proline | 13.35 |
| Serine | 10.16 |
| Tyrosine | 0.50 |
| Tryptophan | 3.20 |
| Amino Acid (g/l) Total | 200.00 |

3. The stable amino acid solution of claim 1 wherein the amino acid profile is approximately as follows:

| | (g/l) |
|---|---|
| Leucine | 10.80 |
| Isoleucine | 10.80 |
| Valine | 14.40 |
| Glutamic Acid | 10.20 |
| Aspartic Acid | 6.00 |
| Lysine | 13.50 |
| Histidine | 11.80 |
| Arginine | 19.60 |
| Phenylalanine | 10.00 |
| Methionine | 7.60 |
| Threonine | 9.80 |
| Alanine | 27.60 |
| Glycine | 20.60 |
| Proline | 13.40 |
| Serine | 10.16 |

-continued

|  | (g/l) |
|---|---|
| Tyrosine | 0.50 |
| Tryptophan | 3.20 |
| Amino Acid (g/l) Total | 200.00 |

4. The stable amino acid solution of claim 1 wherein the amino acid profile is approximately as follows:

|  | (g/l) |
|---|---|
| Leucine | 10.50 |
| Isoleucine | 11.50 |
| Valine | 18.00 |
| Glutamic Acid | 9.95 |
| Aspartic Acid | 5.85 |
| Lysine | 13.60 |
| Histidine | 11.51 |
| Arginine | 19.10 |
| Phenylalanine | 9.75 |
| Methionine | 7.41 |
| Threonine | 9.56 |
| Alanine | 26.90 |
| Glycine | 20.09 |
| Proline | 13.07 |
| Serine | 9.95 |
| Tyrosine | 0.50 |
| Tryptophan | 3.20 |
| Amino Acid (g/l) Total | 200.00 |

5. The stable amino acid solution of claim 1 wherein the amino acid profile is approximately as follows:

|  | (g/l) |
|---|---|
| Leucine | 10.50 |
| Isoleucine | 11.50 |
| Valine | 18.00 |
| Glutamic Acid | 10.20 |
| Aspartic Acid | 6.00 |
| Lysine | 13.50 |
| Histidine | 11.80 |
| Arginine | 19.60 |
| Phenylalanine | 9.60 |
| Methionine | 7.30 |
| Threonine | 9.40 |
| Alanine | 26.50 |
| Glycine | 19.75 |
| Proline | 12.85 |
| Serine | 9.80 |
| Tyrosine | 0.50 |
| Tryptophan | 3.20 |
| Amino Acid (g/l) Total | 200.00 |

6. The stable amino acid solution of claim 1 wherein the amino acid profile is approximately as follows:

|  | (g/l) |
|---|---|
| Leucine | 10.50 |
| Isoleucine | 11.50 |
| Valine | 18.00 |
| Glutamic Acid | 9.20 |
| Aspartic Acid | 4.00 |
| Lysine | 13.60 |
| Histidine | 11.90 |
| Arginine | 19.80 |
| Phenylalanine | 9.00 |
| Methionine | 6.50 |
| Threonine | 9.90 |
| Alanine | 27.80 |
| Glycine | 20.80 |
| Proline | 13.50 |
| Serine | 10.30 |
| Tyrosine | 0.50 |
| Tryptophan | 3.20 |
| Amino Acid (g/l) Total | 200.00 |

7. The stable amino acid solution of claim 1 wherein branched chain amino acids comprise at least 18% (wt/wt) of the amino acids.

8. A nutritionally useful amino acid solution comprising:
approximately 18 to about 22% branched chain amino acids (wt/wt); and
a total amino acid concentration equal to or greater than 18% (wt/vol); and wherein
the solution further includes nonbranched chain ionic and nonionic amino acids, the ratio (wt/wt) of the nonbranched nonionic to nonbranched chain ionic amino acids being 0.57 to 0.65.

9. The nutritionally useful amino acid solution of claim 8 wherein the total amino acid concentration is 20% (wt/vol) and the branched chain amino acids comprise approximately 18% (wt/wt).

10. The nutritionally useful amino acid solution of claim 8 wherein the total amino acid concentration is 20% (wt/vol) and the branched chain amino acids comprise approximately 20% (wt/wt).

11. A stable high concentration amino acid solution having a nutritionally useful amino acid profile comprising:
at least the amino acids leucine, isoleucine, valine, glutamic acid, aspartic acid, lysine, histidine, arginine, phenylalanine, methionine, threonine, alanine, glycine, proline, serine;
the ratio (wt/wt) of glutamic acid, aspartic acid, lysine, histidine, and arginine to phenylalanine, methionine, threonine, alanine, glycine, proline, and serine being 0.57 to 0.65; and
the ratio of (wt/wt) of glutamic acid, aspartic acid, lysine, histidine, and arginine to phenylalanine, methionine, threonine, alanine, glycine, proline, serine, leucine, isoleucine, and valine being approximately 0.45.

12. A stable high concentration amino acid solution having a nutritionally useful amino acid profile comprising:
at least 18% (wt/vol) amino acid concentration;
excluding amino acids not present in an amount greater than 2% (wt/wt) and branched chain amino acids; the ratio (wt/wt) of amino acids present in the solution having an isoelectric point of 5–7 to amino acids present in the solution having an isoelectric point outside the range of 5–7 being 0.57 to 0.65.

13. The stable high concentration amino acid solution of claim 12 wherein the ratio is 0.62 (wt/wt) and the amino acid concentration is approximately 20%.

14. The stable high concentration amino acid solution of claim 12 wherein the amino acids comprise approximately 18% (wt/wt) branched chain amino acids.

15. The stable high concentration amino acid solution of claim 12 wherein the amino acids comprise approximately 20% (wt/wt) branched chain amino acids.

* * * * *